US006750664B2

United States Patent
Lance et al.

(10) Patent No.: US 6,750,664 B2
(45) Date of Patent: Jun. 15, 2004

(54) APPARATUS FOR MANAGING AN INTERGRATED CIRCUIT

(75) Inventors: Philippe Lance, Toulouse (FR); Philippe Meunier, Cugnaux (FR)

(73) Assignee: Freescale Semiconductor, Inc., Austin, TX (US)

( * ) Notice: Subject to any disclaimer, the term of this patent is extended or adjusted under 35 U.S.C. 154(b) by 0 days.

(21) Appl. No.: 09/934,159

(22) Filed: Aug. 21, 2001

(65) Prior Publication Data

US 2002/0021239 A1 Feb. 21, 2002

(51) Int. Cl.⁷ .......................... G01R 27/08; G01R 27/26
(52) U.S. Cl. ...................... 324/721; 324/765; 324/670; 324/760; 713/300; 713/324
(58) Field of Search ................................ 324/760, 670, 324/721, 685, 765, 158.1; 257/706, 467; 323/907; 713/300

(56) References Cited

U.S. PATENT DOCUMENTS

| | | | |
|---|---|---|---|
| 3,868,508 A | 2/1975 | Lloyd .......................... 250/330 |
| 5,201,841 A | 4/1993 | Lebeau et al. .................. 364/5 |
| 5,237,481 A * | 8/1993 | Soo et al. ..................... 361/103 |
| 5,477,076 A | 12/1995 | Gay et al. .................... 257/467 |
| 5,829,879 A | 11/1998 | Sanchez et al. ............. 374/178 |
| 6,415,858 B1 * | 7/2002 | Getchel et al. ............. 165/206 |

FOREIGN PATENT DOCUMENTS

| | | | |
|---|---|---|---|
| WO | WO 98/34101 | 8/1998 | .......... G01N/25/72 |
| WO | WO 00/40985 | 7/2000 | .......... G01R/31/309 |

OTHER PUBLICATIONS

EP 00402329 European Search Report, 3 pgs Mar. 22, 2001.
Kallis, "Nondestructive Infrared Inspection of Hybrid Microcircuit Substrate–to–Packge Thermal Adhesive Bonds," IEEE Transactions on Components, Hybrids, and Manufacturing Technology, vol. CHMT–4, No. 3, Sep. 1981, 4 pp.

* cited by examiner

Primary Examiner—N. Le
Assistant Examiner—Donald M Lair
(74) Attorney, Agent, or Firm—Robert L. King

(57) ABSTRACT

An apparatus for an integrated circuit comprising a thermal sensor (41–44), an A-D converter (58) coupled to the thermal sensor, wherein the thermal sensor provides an input to the A-D converter, and the A-D converter converts the input to a digital value representative of the thermal environment of the thermal sensor. The integrated circuit collects a data value at a location on an integrated circuit wherein the data value has a predetermined functional relationship to the temperature at the location. The integrated circuit converts the data value to a value representative of the thermal environment of the location on the integrated circuit.

14 Claims, 3 Drawing Sheets

APPARATUS FOR MANAGING AN INTERGRATED CIRCUIT

FIELD OF THE INVENTION

The present invention relates generally to managing integrated circuits, and for example, managing integrated circuits in response to a thermal reading of a location on the integrated circuit.

BACKGROUND OF THE DISCLOSURE

Certain semiconductor devices that generate a significant amount of heat use a heatsink in order to dissipate excess heat. Solder is generally used to connect the semiconductor substrate to the heat sink. It is not uncommon to have voids in the solder between the semiconductor substrate and the heatsink. If these voids are located under portions of the semiconductor substrate which generate significant amounts of heat, the reliability of the semiconductor device may be significantly impacted. Having a void between the semiconductor die and the heatsink will significantly increase the thermal resistance between the semiconductor die and the heatsink at the location of the void. As a result of the increased thermal resistance, the temperature at that location of the semiconductor die will be much higher than if a void had not been present. The higher localised temperatures on the semiconductor die may produce failures in the semiconductor die during normal operation in a system. In addition to the voids that may be present in the solder connecting the semiconductor die and the heatsink, the heatsink may be physically connected to a printed circuit board by way of a second layer of solder. This second layer of solder may also have voids which increase the thermal resistance between the semiconductor die and the printed circuit board at the location of the void. As a result of the increased thermal resistance, the temperature at that location of the semiconductor die will be much higher than if a void in the second layer of solder had not been present. The higher localised temperatures on the semiconductor die may produce failures in the semiconductor die during normal operation in a system. Thus, a void in the solder layer between the semiconductor die and the heatsink or the solder layer between the heatsink and the printed circuit board will result in an increased temperature at the corresponding location on the semiconductor die. It would be very helpful to be able determine if there are solder voids present that seriously impact the reliability of the semiconductor die.

BRIEF DESCRIPTION OF THE DRAWINGS

Embodiments of the invention will now be more fully described, by way of example, with reference to the drawings, of which.

DETAILED DESCRIPTION OF EMBODIMENTS OF THE INVENTION

A. Description of the Figures

Figure 1:
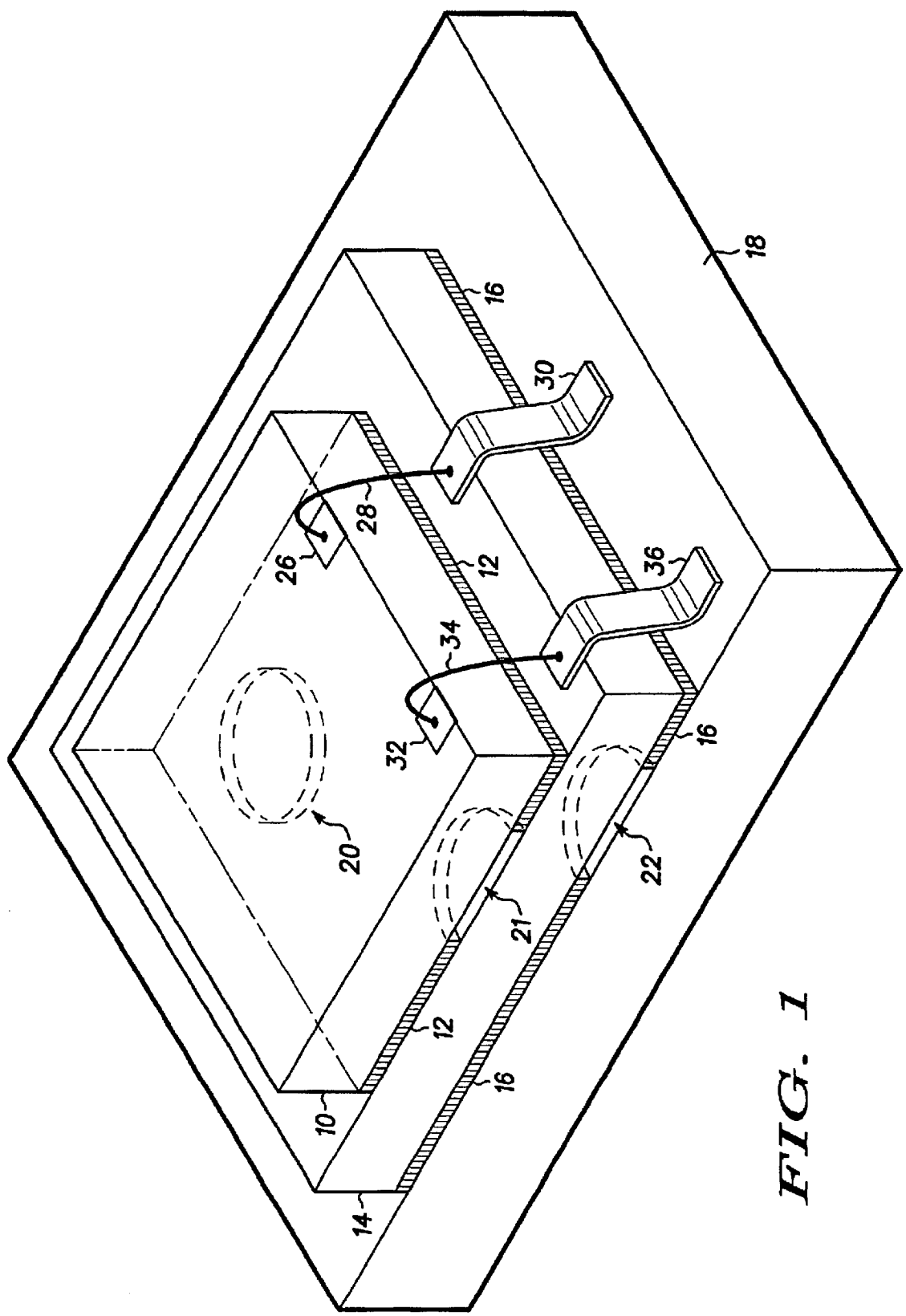
FIG. 1 shows a perspective view of an integrated circuit according to one embodiment of the invention.

FIG. 1 illustrates a semiconductor die 10 which is connected to a copper heatsink 14 by way of solder 12. Although heatsink 14 has been illustrated as being composed of copper, alternate materials which conduct heat may be used. Heatsink 14 is connected to aluminium/copper heatsink 18 on a printed circuit board by way of solder 16. Although printed circuit board/heatsink 18 has been illustrated as being composed of aluminium and copper, alternate materials which conduct heat may be used. Voids 20 and 21 in solder 12 have been illustrated to show that it is relatively common in the manufacturing process for voids to develop in solder 12 between semiconductor die 10 and heatsink 14. Similarly void 22 in solder 16 has been illustrated to show that it is relatively common in the manufacturing process for voids to develop in solder 16 between heatsink 14 and heatsink 18. Integrated circuit pads 26 and 32, bonding wires 28 and 34, and integrated circuit pins 30 and 36 have been illustrated as examples of how semiconductor die 10 may be electrically coupled to the printed circuit board containing heatsink 18 in a standard prior art manner.

Figure 2:
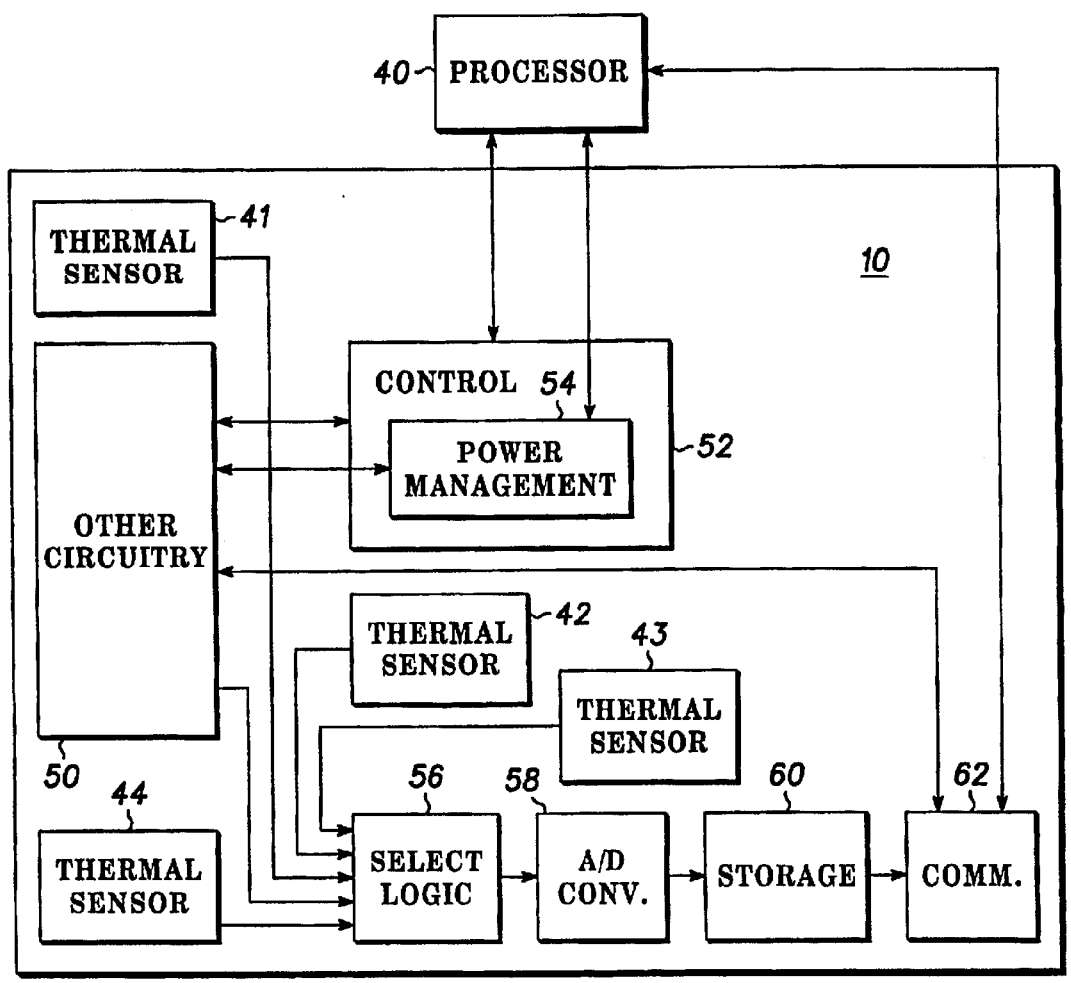
FIG. 2 shows a schematic block diagram of an integrated system according to one embodiment of the invention.

FIG. 2 illustrates one embodiment of semiconductor die 10. Semiconductor die 10 includes thermal sensors 41–44, other circuitry 50, control circuitry 52, power management circuitry 54, select logic 56, analog to digital converter 58, storage circuitry 60, and communication circuitry 62. In one embodiment of the present invention a processor 40 is located external to semiconductor die 10. However, in alternate embodiments of the present invention processor 40 may be located on semiconductor die 10. Note that processor 10 may be any type of processing device, including, for example, a computer, a tester used for testing semiconductor devices, an integrated circuit which is capable of performing a processing function, a microcontroller, etc.

In the embodiment of the present invention illustrated in FIG. 2, thermal sensors 41–44 are coupled to select logic 56 to provide an input to select logic 56. Select logic 56 is coupled to analog digital converter 58 to provide an analog input to analog to digital converter 58. Analog to digital converter 58 is coupled to storage circuitry 60 to provide a digital value to storage circuitry 60. Storage circuitry 60 is coupled to communication circuitry 62 to provide the digital value which it was storing to communication circuitry 62. Communication circuitry 62 is bi-directionally coupled to processor 40 in order to provide the digital value from communication circuitry, as well as to communicate other information between processor 40 and semiconductor die 10. In some embodiments of the present invention, communication circuitry 62 is also bi-directionally coupled to other circuitry 50 in order to provide and receive other information from processor 40. In some embodiments of the present invention, select logic 56 may additionally receive one or more inputs from other circuitry 50. In some embodiments of the present invention, control circuitry 52 includes power management circuitry 54. Both control circuitry 52 and power management circuitry 54 are bi-directionally coupled to other circuitry 50. Processor 40 is also bi-directionally coupled to control circuitry 52 and power management circuitry 54.

Figure 3:
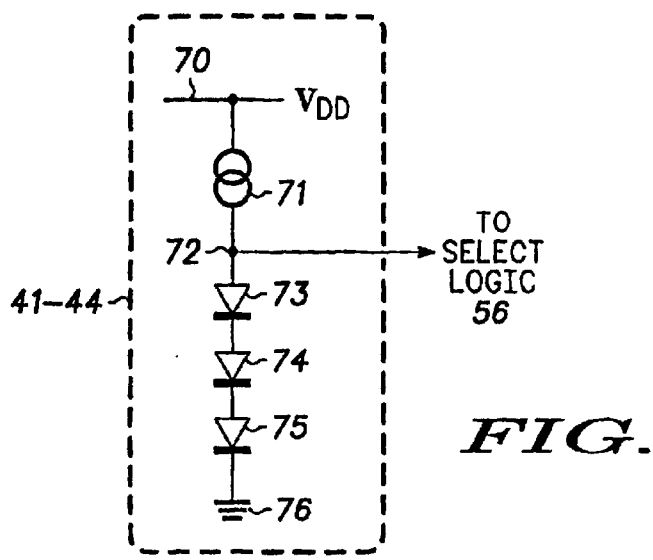
FIG. 3 shows a schematic block diagram of an embodiment of a thermal sensor.

FIG. 3 illustrates one embodiment of thermal sensor 41, 42, 43, and 44 of FIG. 2. Note that various embodiments of semiconductor die 10 of FIG. 2 may include any number of thermal sensors which may or may not be the same. FIG. 3 illustrates just one possible embodiment of thermal sensors 41–44. Alternate embodiments of the present invention may use one or more various embodiments of thermal sensors on semiconductor die 10. The particular embodiment of thermal sensors 41–44 illustrated in FIG. 3 includes a current source 71 having a first terminal coupled to a power supply voltage 70, and having a second terminal coupled to a node 72. Node 72 is coupled to a first current electrode of diode 73. A second current electrode of diode 73 is coupled to a first current electrode of diode 74. A second current electrode of diode 74 is coupled to a first current electrode of diode 75. A second current electrode of diode 75 is coupled to a power supply voltage 76. Note that the power supply voltage 70 is at a higher voltage potential than power supply voltage 76. The voltage at node 72 is provided to select logic 56.

Figure 4:
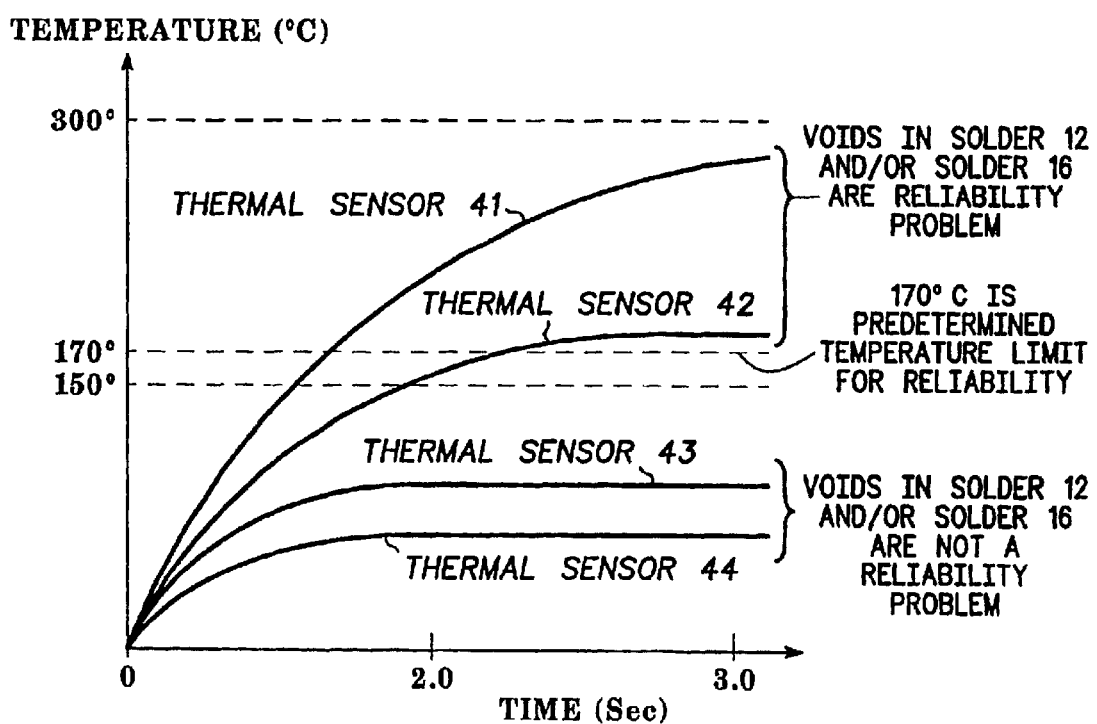
FIG. 4 is a graph showing temperature versus time response for thermal sensors depicted in FIGS. 2 and 3.

FIG. 4 illustrates a graph of temperature versus time for thermal sensors 41–44 (see FIGS. 2 and 3). In order to generate the graph illustrated in FIG. 4, a predetermined power is applied at the location of each of thermal sensors 41–44. A parameter of thermal sensors 41–44 is then measured, such as the voltage at node 72 (see FIG. 3), in order to determine the temperature of the semiconductor die 10 at the location of each thermal sensor 41–44.

B. Description of Operation

Referring to FIG. 2, in one embodiment of the present invention at least one thermal sensor 41–44 is located on semiconductor die 10 in order to monitor the local thermal resistance at that particular location on semiconductor 10. The detection of a high local thermal resistance may then be used to select which ones of a plurality of semiconductor dice 10 may be considered to have a reliability problem due to potential voids in solder 12 or solder 16 (see FIG. 1). Of course, although this embodiment is directed to a semiconductor die, alternate embodiments of the present inventive semiconductor die 10, may alternately be any type of substrate, not necessarily semiconductors, integrated thereon.

Some embodiments of the present invention may use only one thermal sensor (e.g. 41), however alternate embodiments of the present invention may use any number of thermal sensors distributed in various selected locations on semiconductor die 10. The location of thermal sensors 41–44 on semiconductor die 10 may be selected in a wide variety of ways, from a random selection to selection based on predetermined parameters. For example, computer modelling of the thermal resistance of semiconductor die 10 using any known modelling techniques (e.g. extracted from the layout of circuitry on semiconductor die 10) may be used to select critical areas or locations on semiconductor die 10. One or more of these critical areas, which can be determined using known modelling techniques for thermal resistance, may then be made the location sites for thermal sensors 41–44. Again, note that any number of thermal sensors 41–44 may be used on the semiconductor die 10.

Although semiconductor die 10 has been illustrated as having a plurality of identical thermal sensors 41–44 (see FIG. 3), alternate embodiments of the present invention may use the same or different circuitry to implement any number of thermal sensors on semiconductor die 10. Thus all, some, or none of the thermal sensors on a semiconductor die 10 may use the same circuit. Similarly, all, some, or none of the thermal sensors on a semiconductor die 10 may use the same physical layout.

Referring to FIG. 3, as the temperature of semiconductor die 10 at the location of thermal sensor 41 increases, the voltage at node 72 decreases in a linear fashion. This voltage at node 72 is provided to analog to digital converter 58 by way of select logic 56. Select logic 56 performs a multiplexing function to select which one of a plurality of inputs to analog to digital converter 58 is provided at a particular time. The voltage from node 72 is then converted by analog to digital converter 58 into a digital value. Note that the circuit configuration of thermal sensors 41–44 may optionally be selected so that the input value provided from the thermal sensors 41–44 to the analog to digital converter 58 is in the mid range of analog to digital converter 58 in order to increase the accuracy of the analog to digital conversion.

Analog to digital converter 58 converts the analog value provided by one of thermal sensors 41–44 and provides the corresponding digital value to storage circuitry 60. Note that alternate embodiments of the present invention may not use storage circuitry 60 but may directly provide the digital value from analog to digital converter 58 to another circuitry element or device such as communication circuitry 62 or processor 40. In one embodiment of the present invention storage circuitry 60 may be a register within the memory map of semiconductor die 10. In alternate embodiments of the present invention, storage circuitry 60 may be any type of circuitry which is capable of storing a digital value. Communication circuitry 62 then provides the digital value produced by analog to digital converter 58 to processor 40.

In one embodiment of the present invention, processor 40 may use the information from thermal sensors 41–44 to provide temperature management back to semiconductor die 10. Processor 40 may provide this feedback to semiconductor die 10 in a variety of ways. For example processor 40 may provide feedback information to semiconductor die 10 by way of power management circuitry 54. Alternately, this feedback information for temperature management may be provided from processor 40 to semiconductor die 10 by way of communication circuitry 62. The feedback from processor 40 may affect semiconductor die 10 in any pre-selected manner that is determined to be beneficial to semiconductor die 10. For example, the feedback from processor 40 may be used to lower the temperature at the location of thermal sensors 41–44, or alternately to lower the temperature in a predetermined desired manner based on the inputs provided by thermal sensors 41–44. For example, processor 40 may reduce the power in specific locations of other circuitry 50, or alternately may change the frequency at which portions of other circuitry 50 operates. In one embodiment of the present invention, the temperature management feedback provided by processor 40 may be used to reduce the temperature at the locations of thermal sensors 41–44, which locations have been previously identified as critical areas.

FIG. 4 illustrates a graph of temperature versus time that may be generated from a semiconductor die 10 having thermal sensors 41–44. At time 0, a predetermined power is applied at the various locations of thermal sensors 41–44. The voltage level at node 72 for each one of thermal sensors 41–44 is then measured by analog to digital converter 58, and the resulting digital value is provided to processor 40 by way of communication circuitry 62. Using the known power applied and the resulting voltage at node 72, processor 40 may calculate the temperature at the location of each one of thermal sensors 41–44. The temperature at the location of each of thermal sensors 41–44 is a function of the thermal resistance and the power. Note that the thermal resistance is linearly related to the voltage measured at node 72. In one embodiment of the present invention, the thermal resistance at the location of each of thermal sensors 41–44 is calculated by the following equation:

$$\textit{Thermal Resistance} = [(\textit{Vmeasured} - \textit{Vambient}) \times K]/\textit{POWER}$$

where Vmeasured is the digital value of the voltage measured at node 72 after the predetermined power is applied, Vambient is the digital value of the voltage measured at node 72 for a known temperature such as ambient room temperature, K is a predetermined constant which is known (e.g. for a diode formed in silicon, K=6 millivolts/degrees Celsius), and POWER is the known power that is applied at the location of that particular one of thermal sensors 41–44. The value of the resulting thermal resistance which is calculated by processor 40 can be used to determine whether there is a potential reliability problem with semiconductor die 10. If the thermal resistance is too high, semiconductor die 10 has a significant chance of failing during normal operation.

Note that in some embodiments of the present invention it is not necessary to actually determine the temperature or thermal resistance at the location of a particular sensor 41–44. Note that it is possible to determine the thermal resistance in an area of semiconductor die 10 by comparing the outputs of two or more thermal sensors 41–44. For example, by using known modelling techniques as discussed above to place thermal sensors in generally relative cool and hot locations on the semiconductor die, readings from a thermal sensor placed in a cool location may be compared with readings from a thermal sensors placed in a hot location. It is not necessary to actually determine the temperature at a particular location. Thus, the temperature differential, provided by way of the differential between the output of at least two thermal sensors 41–44, may provide the necessary information to determine thermal resistance. A calculation of the actual temperature itself may not be necessary.

Referring to FIG. 4, the actual local temperatures themselves have been illustrated in order to show how a determination can be made as to whether a particular semiconductor die 10 may have a reliability problem based on the data provided by thermals sensors 41–44. In the case illustrated in FIG. 4, 170 degrees Celsius has been selected as a pre-determined temperature limit for the reliability of semiconductor die 10. Alternate embodiments may have other pre-determined temperature limits for the reliability of semiconductor die 10.

As the temperature at the locations of thermal sensors 41 and 42 have exceeded the predetermined limit of 170 degrees Celsius, it is then known that those locations on semiconductor die 10 have a reliability problem most likely due to voids in solder 12 and/or solder 16. Note that the same power stimulus has resulted in lower temperatures at the locations of thermal sensors 43 and 44. Consequently the locations of thermal sensors 43 and 44 most likely do not have voids in solder 12 and or solder 16. And, as a result, the locations of sensors 33 and 34 do not present a reliability problem to semiconductor die 10.

Note that the present invention may be utilised during the testing of semiconductor die 10 in order to determine its future potential reliability. As a result, any semiconductor die 10 which may have potential reliability problems due to voids in solder 12 and/or solder 16 may be screened out before they are sold to a customer and placed in a system. A significant advantage of this pre-screening is that customers do not receive semiconductor die 10 that have significant reliability problems due to voids in solder 12 and/or solder 16. Note that another significant advantage of the invention is that by providing short duration power pulses to semiconductor die 10 the thermal resistance and thus the reliability of semiconductor die 10 can be determined without requiring a significant amount of test time. Referring to FIG. 4, the temperature differential which takes place in the first milliseconds after a predetermined power is applied is sufficient to extrapolate whether or not a void, and thus a reliability problem, exists. Also, note that the present invention allows the measurement of localised temperature spikes or transients, as well as the steady state temperature at a particular location.

Still referring to FIG. 4, note that if a series of voltage values from thermal sensors 41–44 are made over a several millisecond period of time, it is possible to effectively determine the thermal resistance between semiconductor die 10 and heatsink 14, and between heatsink 14 and printed circuit board/heatsink 18, as well as the possibly faulty area (see FIG. 1). The manner in which this is done will now be described. The time required for heat to transfer within semiconductor die 10, within solder 12, within copper heatsink 14, within solder 16, and within heatsink 18 is known based on the materials forming these compounds. Using the calculated temperature at the locations of thermal sensors 41–44 over a period of time (i.e. several milliseconds) it is possible to determine the thermal resistance of the various layers of solder 12, heatsink 14, solder 16 and heatsink 18. If the thermal resistance of a particular layer or interface is much higher than expected, it is likely that there is a void in the solder between those two layers. It is thus possible to determine, from the value of the thermal sensor (e.g. 41) at a particular location whether there is a void in one or more of the underlying solder layers 12, 16, and if so, which solder layer(s) in fact have the void.

It will be appreciated that although the particular embodiments of the invention have been described above, various other modifications and improvements may be made by a person skilled in the art without departing from the scope of the present invention.

What is claimed is:

1. An integrated circuit die comprising:

a plurality of thermal sensors positioned at predetermined differing positions within the integrated circuit die;

an A-D converter coupled to the plurality of thermal sensors, wherein each of the plurality of thermal sensors provides an input to the A-D converter, and the A-D converter converts the input to a digital value representative of the thermal environment of at each location where the plurality of thermal sensors are located; and power management circuitry for selectively modifying voltage or frequency of operation for circuitry in close proximity to the at least one of the predetermined differing positions within the integrated circuit in response to the thermal environment of the at least one of the predetermined differing positions.

2. An integrated circuit as claimed in claim 1 wherein the each of the plurality of thermal sensors comprises at least one diode.

3. An integrated circuit as claimed in claim 2 wherein each of the plurality of thermal sensors comprises a plurality of diodes wherein each diode in the plurality is coupled in series.

4. An integrated circuit as claimed in claim 3 wherein the plurality of diodes comprises three diodes.

5. An integrated circuit as claimed in claim 1 further comprising:

select logic circuitry coupled to each of the plurality of thermal sensors and to the A-D converter for selectively coupling each of the plurality of thermal sensors to the A-D converter.

6. An integrated circuit as claimed in claim 5 wherein the plurality of thermal sensors are positioned on the integrated circuit in accordance to at least one predetermined criteria.

7. An integrated circuit as claimed 6 wherein a predetermined criteria is sensitivity to thermal resistance.

8. An integrated circuit as claimed in claim 1 further comprising communication circuitry and a processor electrically coupled to the A-D converter, the processor receiving the data value from the communication circuitry, and providing control information to control the power management circuitry.

9. An integrated circuit as claimed in claim 8 further comprising storage circuitry coupled between the A-D converter and the communication circuitry for storing the digital value.

10. An integrated circuit as claimed in claim 8 wherein the processor is not physically within the integrated circuit.

11. An integrated circuit comprising:

a plurality of thermal sensors positioned at predetermined differing positions within the integrated circuit die, each of the plurality of thermal sensors providing a sense voltage;

select circuitry coupled to the plurality of thermal sensors for selectively providing the sense voltage of each of the plurality of sensors at an output thereof;

an A-D converter coupled to the output of the select circuitry, the A-D converter converting each sense voltage to a digital value representative of the thermal environment at each location where the plurality of thermal sensors are located;

a storage circuit coupled to the A-D converter for storing the digital value;

communication circuitry coupled to the storage circuit for communicating the digital value; and power management circuitry for selectively modifying voltage or frequency of operation for circuitry in close proximity to the at least one of the predetermined differing positions within the integrated circuit in response to the thermal environment of the at least one of the predetermined differing positions.

12. The integrated circuit of claim 11 further comprising:

a processor coupled to the communication circuitry and to the power management circuit, the processor determining whether the digital value exceeds a predetermined threshold value in order to determine whether to control the power management circuitry to modify voltage or frequency of operation for the circuitry in close proximity to the at least one of the predetermined differing positions.

13. The integrated circuit of claim 12 wherein the processor is located on the integrated circuit.

14. An integrated circuit comprising:

thermal sensing means positioned at predetermined differing positions within the integrated circuit die, each of the thermal sensing means providing a sense voltage;

selection means coupled to the thermal sensing means for selectively providing the sense voltage of each of the thermal sensing means at an output thereof;

A-D conversion means coupled to the output of the selection means, the A-D conversion means converting each sense voltage to a digital value representative of the thermal environment at each location where the thermal sensing means are located;

storage means coupled to the A-D conversion means for storing the digital value;

communication means coupled to the storage means for communicating the digital value; and power management means for selectively modifying voltage or frequency of operation for circuitry in close proximity to the at least one of the predetermined differing positions within the integrated circuit in response to the sense voltage sensed at the at least one of the predetermined differing positions.

* * * * *

UNITED STATES PATENT AND TRADEMARK OFFICE
CERTIFICATE OF CORRECTION

PATENT NO. : 6,750,664 B2
DATED : June 15, 2004
INVENTOR(S) : Philippe Lance et al.

It is certified that error appears in the above-identified patent and that said Letters Patent is hereby corrected as shown below:

Column 6,
Line 37, delete "environment of at" and replace with -- environment at --.
Line 66, delete "as claimed 6" and replace with -- as claimed in claim 6 --.

Signed and Sealed this

Eighteenth Day of October, 2005

JON W. DUDAS
*Director of the United States Patent and Trademark Office*